United States Patent [19]

Pohl

[11] Patent Number: 5,322,301
[45] Date of Patent: Jun. 21, 1994

[54] CHUCKING TOOL WITH A WEDGING ACTION FOR TESTING MACHINES

[75] Inventor: Andreas Pohl, Gross-Umstadt, Fed. Rep. of Germany

[73] Assignee: Carl Schenck AG, Darmstadt, Fed. Rep. of Germany

[21] Appl. No.: 939,457

[22] Filed: Sep. 2, 1992

[30] Foreign Application Priority Data

Dec. 5, 1991 [EP] European Pat. Off. ......... 91120868.4

[51] Int. Cl.$^5$ .............................................. G01N 3/04
[52] U.S. Cl. .................................... 279/4.06; 73/831; 73/857; 279/74
[58] Field of Search ................. 73/831, 833, 846, 853, 73/856, 857, 859, 860; 279/4.01, 4.04, 4.06, 4.12, 74, 121

[56] References Cited

U.S. PATENT DOCUMENTS 3,335,603  8/1967  Gram .

FOREIGN PATENT DOCUMENTS

| 0257104 | 3/1988 | European Pat. Off. . |
| 0300702 | 1/1989 | European Pat. Off. . |
| 1977205 | 1/1968 | Fed. Rep. of Germany . |
| 2141566 | 3/1973 | Fed. Rep. of Germany . |
| 8529717 | 3/1986 | Fed. Rep. of Germany . |
| 74636 | 6/1981 | Japan ....................... 73/859 |
| WO83/03003 | 9/1983 | PCT Int'l Appl. . |

*Primary Examiner*—Steven C. Bishop
*Attorney, Agent, or Firm*—W. G. Fasse; W. F. Fasse

[57] ABSTRACT

A clamping or chucking tool for clamping a test sample in a testing machine has a clamping housing for applying a wedging action to the sample with the aid of one or two clamping jaws that are activated by an operating member that is inserted into the clamping housing and axially displaceable in the clamping housing. The clamping jaws are slidingly guided in a V-groove of the operating member but are stationary in the axial direction of the clamping housing, while the operating member is movable axially relative to the clamping housing for imparting to the clamping jaws a radial movement component perpendicularly to the longitudinal axis of the test sample. Lateral guide arms engage respective guide grooves in the clamping jaws to hold the clamping jaws against axial movement while permitting the radial movement. The clamping housing and the operating member are provided with at least one lateral opening for a rapid insertion of the test sample laterally into the clamping housing. This type of construction provides a chucking tool for holding test samples that may be exposed to tension loads, or to compression loads and/or to torque loads.

13 Claims, 5 Drawing Sheets

FIG. 9

CHUCKING TOOL WITH A WEDGING ACTION FOR TESTING MACHINES

FIELD OF THE INVENTION

The invention relates to a chucking tool with a wedging action for holding a work piece, especially a work piece to be tested in a testing machine. Such testing may involve the application of tensile stress, compression stress, and/or torque stress.

BACKGROUND INFORMATION

Clamping devices with a wedging action are known in many different constructions. These constructions fall into three basic types. An open type, a closed type, and a semi-open type are recognized. Such clamping devices are also classified in accordance with the intended type of stress to be applied to a test sample, namely for applying tension stress or for applying compression stress, or for applying tension or compression stress as desired. The construction will differ for the type of stress to be applied to the test sample.

German Patent Publication DE-AS 2,141,566, for example, discloses a clamping device with a wedging action of the open type construction. Such a structure is used exclusively for testing samples with regard to tensile stress, whereby the samples must have either a circular or a rectangular flat cross-sectional configuration. This known clamping device with a wedging action, has a clamping housing with a wedge-shaped clamping mouth formed by respective wedge-shaped clamping elements referred to as wedging clamping jaws mounted in said clamping housing for an axial displacement. Due to the wedge shape of the clamping mouth and of the clamping jaws, the latter generate simultaneously with an axial movement a radially directed clamping movement. In order to apply the clamping action to a test sample, the clamping jaws are operated by a piston cylinder device in an axial direction. In order to again release a test sample from the clamping jaws, the piston cylinder device is depressurized. Tension springs are connected to the clamping jaws in such a way that they counteract the clamping force of the piston cylinder device, whereby the clamping jaws upon depressurizing the piston cylinder device, are returned by the tension springs into the starting position, thereby to release the clamping action.

It is also known from European Patent Publication No.: 0,257,104 to provide a piston cylinder device for opening the clamping jaws by causing a retraction movement of these clamping jaws. In such a structure the clamping housing is constructed so that the sample to be tested can be inserted into the clamping housing in a lateral direction. This feature speeds up and simplifies the clamping operation of the sample. The clamping jaws and the clamping housing in which these jaws are mounted, are so constructed that a self-locking feature of the wedges of the clamping jaws can be utilized by applying a tension force to the sample.

The just described so-called open type of construction of the wedging clamping device has the disadvantage that due to the forces that the clamping housing itself must take up when a sample is loaded, the clamping housing must have relatively large dimensions so as to avoid any elastic reaction of the clamping housing which may result in the release of the test sample. For example, German Utility Model Publication 1,977,205 discloses a structure intended to minimize the elastic reaction of the clamping housing. In order to strengthen the clamping housing, a ring-shaped clamping piece is arranged around the clamping housing and the ring-shaped clamping piece is operable by a hydraulic drive.

U.S. Pat. No. 3,335,603 (Gram) discloses a wedge-type clamping device of the so-called closed construction capable of applying tension loads or compression loads to a test sample. This known clamping device comprises clamping wedges arranged in a housing closed on all sides, except for an axial inlet opening for permitting the insertion of the test sample end into the clamping device. Thus, it is a disadvantage of the closed type of construction that the sample must be inserted in the axial longitudinal direction which requires the axial displacement of at least one of the two clamping devices or clamping heads needed for holding a test sample. Such axial displacement is time consuming and requires additional structural features for performing the axial displacement. However, the closed type of construction has the advantage that it has a small overall structural height due to the closed type construction of the housing.

Another known clamping device is constructed particularly for applying a compression load to a sample. The construction is such that the compression force introduced into the test sample causes a closing of the wedges for applying the clamping action to the sample.

OBJECTS OF THE INVENTION

In view of the foregoing it is the aim of the invention to achieve the following objects singly or in combination:

to provide a chucking tool or clamping device in which a wedging action is applied for holding a sample to be tested and which is universally useable for all types of load application which has a compact structure and permits a rapid clamping, as well as a rapid release of a sample while still being able to take up substantial loads;

to combine the advantages of the above described open type construction with the advantages of the closed type of construction, while avoiding disadvantages of both constructions;

to provide a clamping device which by its structure is especially suitable for automatic testing operations of many test samples in sequence;

to provide different sized piston surfaces for the application of the clamping force and for the application of the release force; and to construct the clamping surfaces that contact a sample to provide a force or form-locking clamping of the sample.

SUMMARY OF THE INVENTION

The clamping device or chucking tool according to the invention is characterized by the following features. An operating member is axially displaceable in a clamping housing to provide a wedging action. The housing axis extends coaxially with a longitudinal axis of a sample to be tested and coaxially with the operating member. One, preferably two clamping jaws are mounted in a V-groove or conical recess in the operating member. Preferably, the clamping jaw or jaws are slideably guided in the V-groove or conical recess. In the preferred embodiment the clamping jaws and the V-groove have respective slants which taper toward the end of a clamped probe. The side of the clamping housing facing toward the probe is provided with a cover that holds the clamping jaws in a form-locking manner against movement in the axial direction while permitting a movement component of the jaws in a direction perpendicularly to the longitudinal axis of the probe. The clamping housing and the operating member are provided with respective lateral openings for a lateral insertion of the probe into the position for clamping by the clamping jaw or jaws.

The just described combination of features combines the advantages of the open-type construction with the advantages of the closed type construction while avoiding their disadvantages. The construction according to the invention permits the insertion of a sample into the space between the clamping jaws or between the clamping jaw and a backing laterally into position, whereby a displacement in the longitudinal direction of the probe is avoided. Additionally the housing can be compact, because the conical recess or V-groove of the operating member is so constructed that the V-groove tapers toward the end of the probe. Form-locking members are provided to hold the clamping jaws stationary relative to the clamping housing in the axial direction, but movable in the clamping housing in the direction perpendicularly to said longitudinal axis of the probe which coincides with the central axis of the housing so that the clamping tool can be used for applying tension and/or compression loads to a sample. Even torque loads can be applied by this type of clamping tool of the invention.

By controlling the activation of the operating member with a pressurized medium, it is possible to control the clamping forces in a simple manner for applying the required loads to a sample. Thus, the testing operation can be automated.

The clamping housing and the operating member are so constructed that two pressure chambers are provided in which one pressure chamber includes a piston ring wall smaller than the piston wall forming part of the other pressure chamber. This arrangement has the advantage that the hydraulic force for clamping the probe can be applied to the large piston surface while the force necessary for releasing the clamping jaws can be applied to the smaller ring surface of the piston.

The preferred embodiment comprises two clamping jaws which provides the most simple possibility for clamping a sample. The surface of the clamping jaws facing and contacting the sample to be tested are provided with surface roughening features, such as grooves and ridges to hold the sample in a force-or form-locking manner.

The housing cover that prevents the clamping jaws from moving axially is preferably so constructed that it also prevents the clamping jaws from rotating about the longitudinal axis, whereby it becomes possible to apply torque loads to a test sample by rotating the entire housing.

BRIEF DESCRIPTION OF THE DRAWINGS

In order that the invention may be clearly understood, it will now be described, by way of example, with reference to the accompanying drawings, wherein.

DETAILED DESCRIPTION OF PREFERRED EXAMPLE EMBODIMENTS AND OF THE BEST MODE OF THE INVENTION

Figure 1:
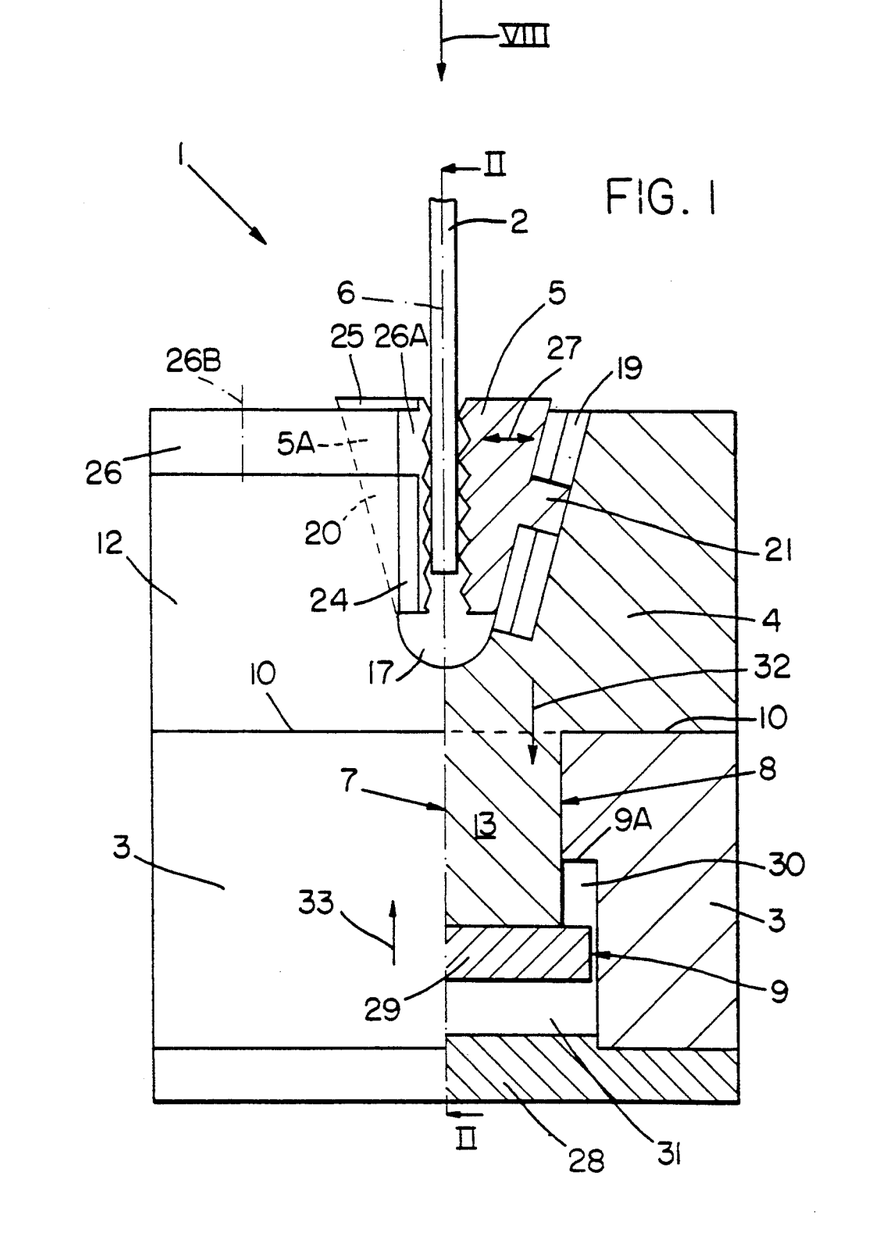
FIG. 1 is a side view and a sectional view of the clamping tool according to the invention, whereby the left-hand side is shown as the side view, while the right-hand side is shown as a sectional view.

FIG. 1 shows the chucking or clamping tool 1 according to the invention which is operated by a pressure medium admitted to respective chambers to be described below. A test sample 2 which has a rectangular cross-section is clamped between two clamping jaws 5 and 5A for applying to the test sample 2 tension loads and/or compression loads and/or torsion loads. The testing machine itself is not shown. However, such a machine would comprise two chucking tools 1 arranged coaxially and mirror-symmetrically to each other. Thus, only one of the chucking tools is shown. The upper, not shown clamping tool is, for example, secured to a cross-beam of a loading frame of the testing machine, while the lower chucking tool 1 shown in FIG. 1 is connected to a loading device not shown. Since the upper and lower clamping or chucking tools are of an identical construction, it is sufficient to describe only one of these tools, for example, the lower tool 1.

Figure 2:
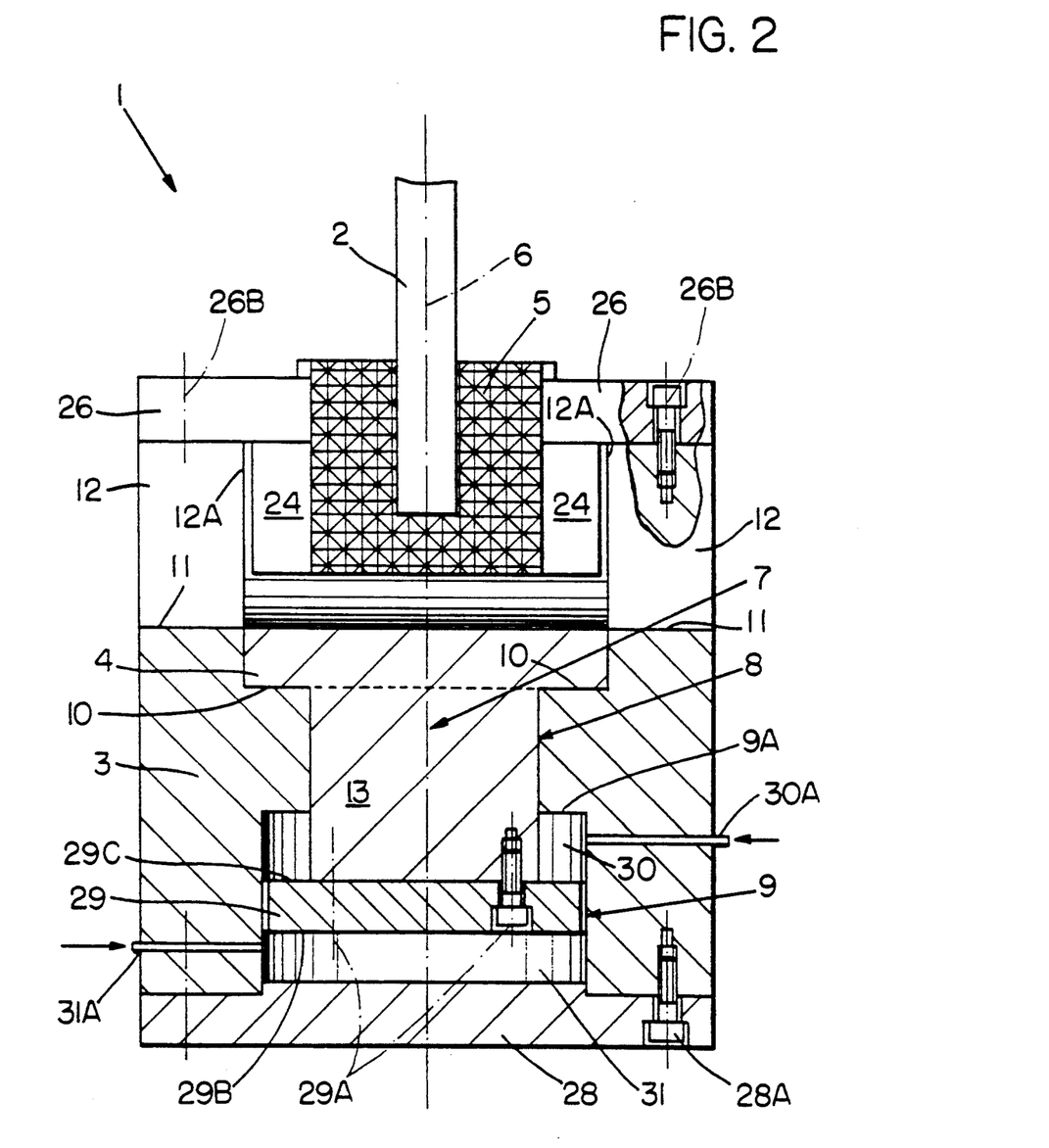
FIG. 2 is a sectional view along section line II—II in FIG. 1, however without running the section through the probe, which is shown in a side view in FIG. 2.

Referring to FIGS. 1 and 2, the chucking tool 1 represented as a lower tool, has a clamping housing 3 with a central bore 8 in which an operating member 4 is guided for axial movement. Two clamping jaws 5 and 5A are received in a V-groove 17 of the operating member, but held against axial displacement as will be described in more detail below. A central housing axis 7 coincides with a central longitudinal axis 6 of a sample 2 to be tested and held between the two clamping jaws 5 and 5A. The clamping housing 3 has a cylindrical configuration and the throughbore 8 coincides with its central axis with the longitudinal cylinder axis 7 of the housing. An axially extending shoulder bore 9 is provided in the lower end of the housing 3 to form a shoulder 9A relative to the central bore 8 for forming a pressure chamber to be described in more detail below.

Figure 8:
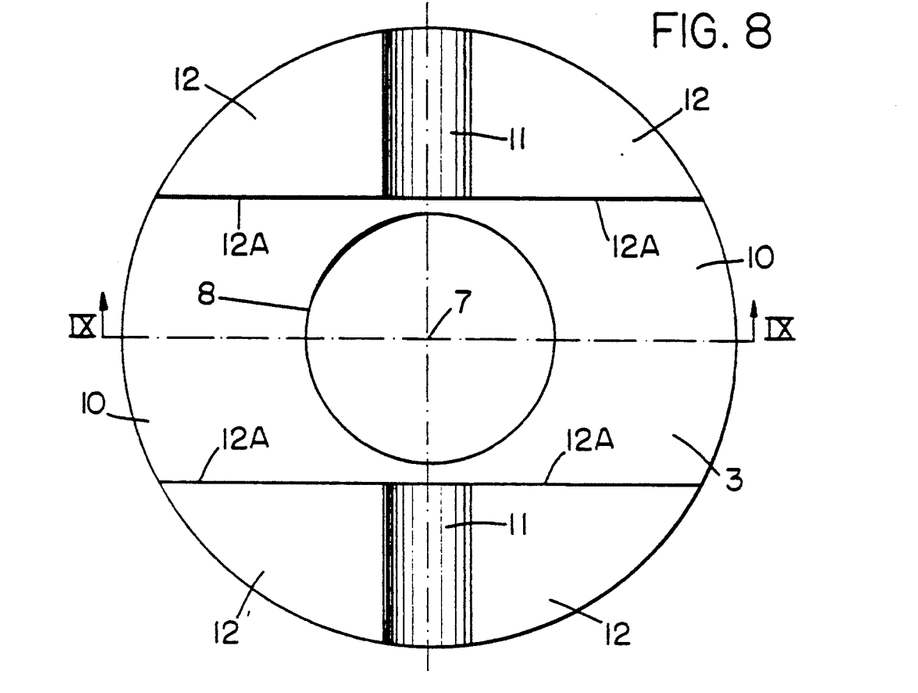
FIG. 8 is a view in the direction of the arrow VIII in FIG. 1, showing the clamping housing, however omitting the clamping jaws and test sample, as well as the operating member shown in FIG. 1.
Figure 9:
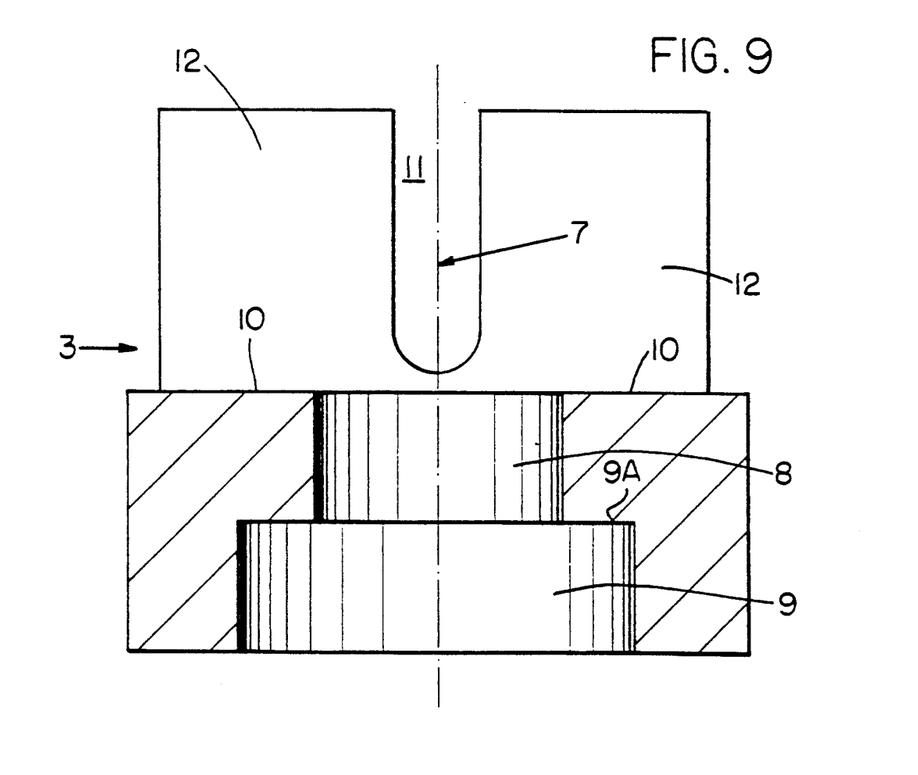
FIG. 9 is a sectional view along the section line IX—IX in FIG. 8, showing the clamping housing.

Referring to FIGS. 8 and 9, the upper portion of the housing 3 is machined to provide four studs 12 separated from one another. The separation is accomplished on the one hand by a channel 10 extending perpendicularly to the longitudinal axis 7 entirely through the upper portion of the housing, and on the other hand, by an access groove 11 extending perpendicularly to the channel 10 and also perpendicularly to the central axis 7, as best seen in FIG. 8. The groove 11 provides access for the sample 2 as will be described below. The width of the channel 10 in the direction of the groove 11 is larger than the diameter of the through-bore 8, so that during the machining initially two segments are formed that are separated by the channel 10. The segments are then divided by the formation or machining of the groove 11 to form the studs 12. It is clear from FIG. 8 that the channel 10 and the groove 11 extend perpendicularly to each other.

Figure 3:
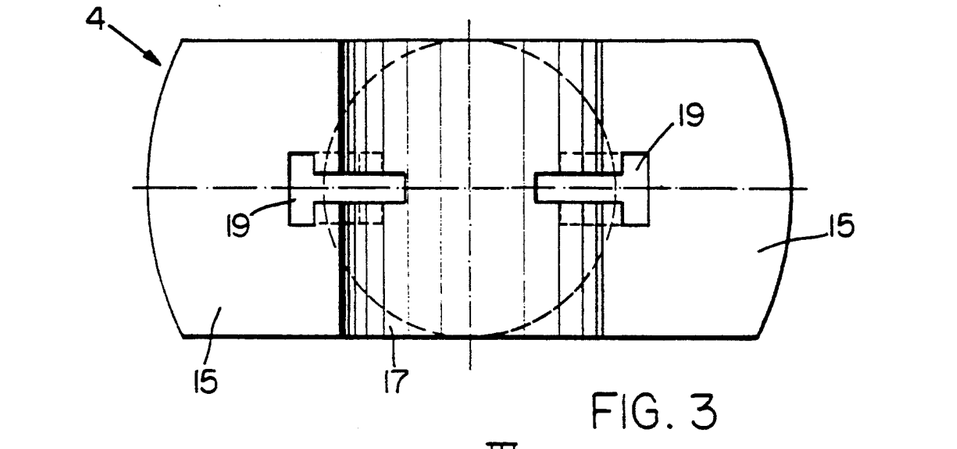
FIG. 3 is a top plan view onto the operating member in the direction of the arrow III in FIG. 4.
Figure 4:
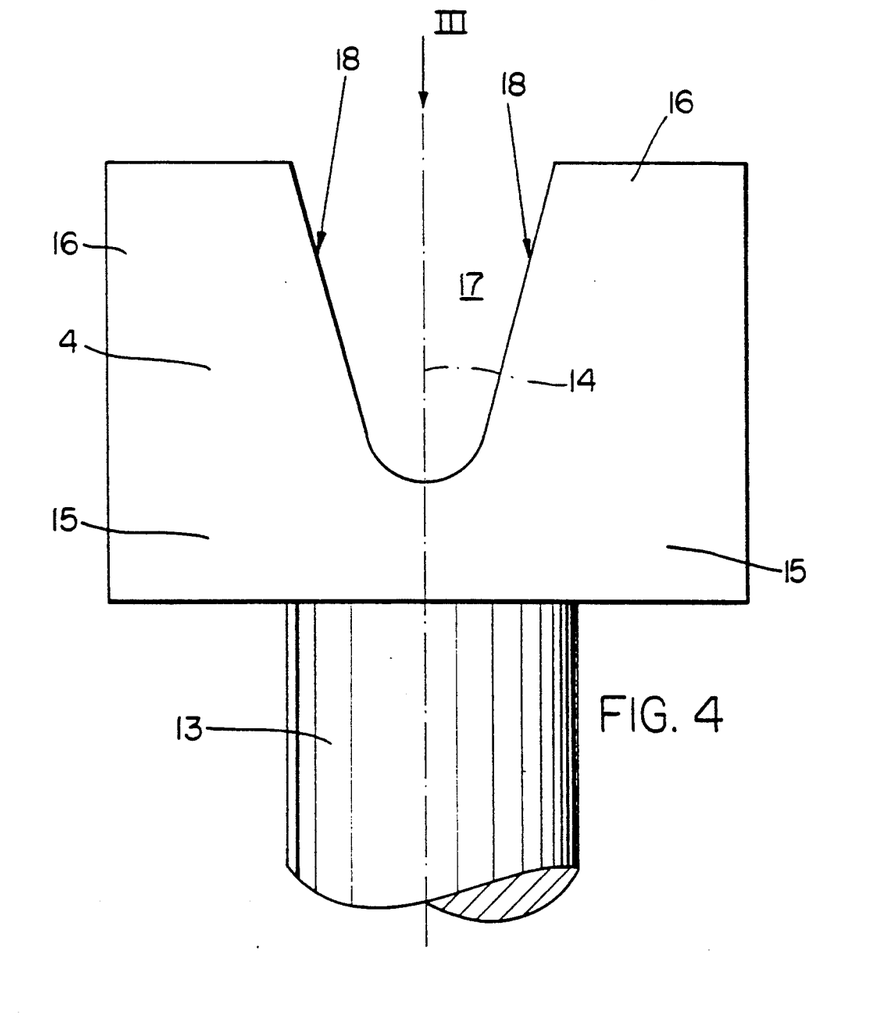
FIG. 4 is a side view of the operating member.

Referring to FIGS. 3 and 4, the operating member 4 will now be described. The operating member 4 is received in the channel 10 as is apparent from FIGS. 1 and 2. The operating member 4 has a cylindrical shaft 13 slidingly fitting into the central bore 8 of the housing 3, whereby the longitudinal central axis 14 of the operating member 4 coincides with the central axis 7 of the housing 3. The upper portion of the operating member 4 comprises radial extensions 15 provided with a central cross-groove of V-configuration 17 between two legs 16. The groove 17 extends entirely through the operating member 4 and has slanted wedging surfaces 18 tapering downwardly in the direction of the end of the sample 2. The shape and size of the operating member 4, especially the radial extension or head portion 15 thereof is adapted to the respective dimensions in the clamping housing 3. In the side walls 18 of the conical V-groove 17, guide grooves 19 shown in FIG. 3, are arranged for guiding the wedging clamping jaws 5, 5A, whereby the latter are slidingly guided in these grooves 19. However, it should be noted that the jaws 5, 5A remain stationary in the axial direction, because they are held by cover arms 26 against an axial displacement, while the operating member 4 moves up as indicated by the arrow 33 in FIG. 1 for a clamping action or down as indicated by the arrow 32 in FIG. 1 for a release action.

Figure 5:
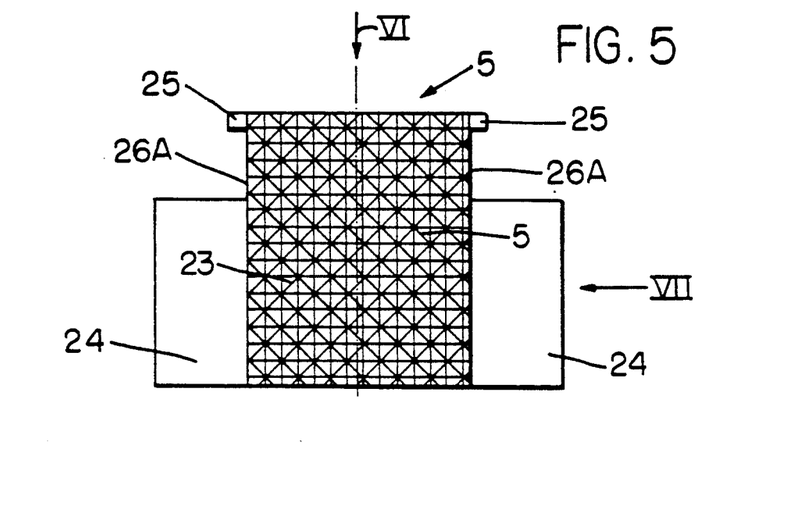
FIG. 5 is a view in the direction as in FIG. 2, however, showing only a side view of the clamping jaw separate from the housing and operating members.
Figure 6:
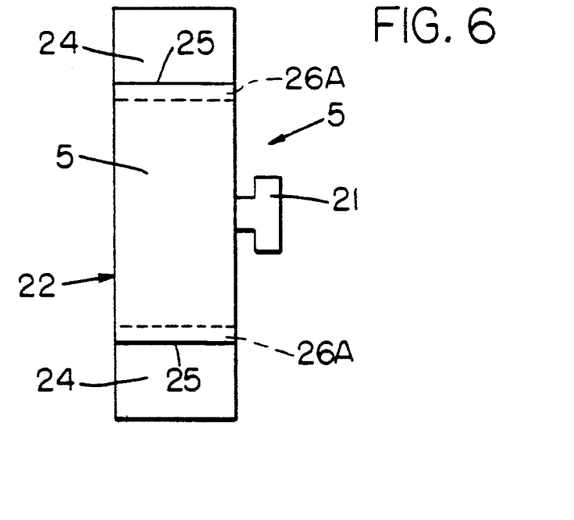
FIG. 6 is a top plan view in the direction of the arrow VI in FIG. 5.
Figure 7:
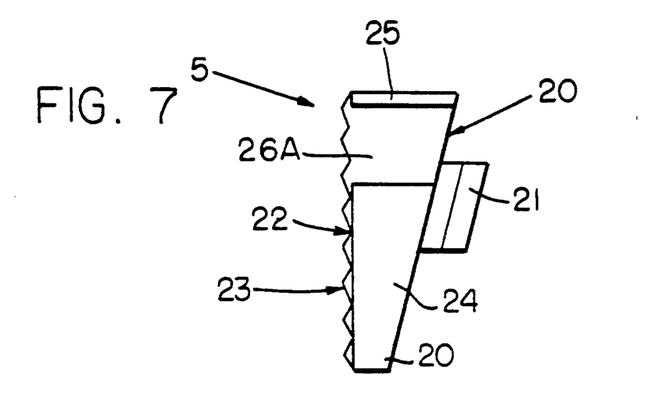
FIG. 7 is a side view of the clamping jaw in the direction of the arrow VII in FIG. 5.

FIGS. 5, 6, and 7 show the clamping jaw 5. The clamping jaw 5A is of the same construction. Both jaws are provided with downwardly slanting slide surfaces 20 that taper in the direction toward the end of the sample 2. The sliding slanted surfaces 20 are adapted to cooperate with the respective slanting surface 18 forming the V-groove 17 in the operating member 4. Each clamping jaw is provided with a guide element 21 preferably having a T-cross-sectional configuration. In any event, the guide element 21 slants in the same direction as the slide surface 20 of the respective jaw 5, 5A. If the guide element 21 has a T-cross-sectional configuration, the respective grooves 19 also forming guide elements will have a T-cross-sectional configuration into which the guide element 21 slidingly fits. However, it should be noted, that other configurations could be used for the guide elements. Incidentally, the grooves 19 slant in the same direction as the surfaces 18 to assure the required cooperation permitting the axial movement of the operating member 4 relative to the clamping jaws 5, 5A which remain axially stationary.

Referring further to FIGS. 5 and 7, the clamping jaws 5, 5A comprise clamping surfaces 22 for holding and clamping the end of the probe 2. For this purpose, the surfaces 22 are provided with grooves 23 between respective ridges for providing a better form-locking and force-locking grip. The sample 2 of FIG. 1 is, as mentioned, a flat sample. Therefore, the respective holding surfaces 22 are extending in parallel to each other. When the sample has a round or rather circular cross-section, the surfaces 22 will be respectively adapted.

As shown in FIGS. 5, 6, and 7, each clamping jaw 5 is provided with lateral extensions 24 forming guide elements that cooperate with surfaces 12A of the studs 12 shown in FIG. 8. In FIG. 2 a slight gap is shown between the guide elements 24 and the surfaces 12A of the studs 12. However, in fact, these guide elements 24 move in a sliding engagement along the surfaces 12A. Additionally, each clamping jaw 5, 5A comprises a top rim 25 that extends laterally over the body of the respective jaw and in parallel to the guide elements 24. Thus, a guide groove 26A is formed on each side of the upper portion of each jaw 5, 5A. Guide arms 26 secured to the respective stud 12 as shown at 26B in FIGS. 1 and 2 engage the respective clamping jaw 5, 5A in these guide grooves 26A. This construction enables the guide arms 26 to prevent a movement of the clamping jaws in a direction coaxially to the longitudinal central axis 7 of the clamping housing 3 while permitting a radial movement component 27 shown in FIG. 1 perpendicularly to the central longitudinal axis 7. This engagement between the guide arms 26 and the jaws in the guide grooves 26A is a form-locking engagement that permits the sliding movement component 27 but prevents axial jaw movement.

Due to the insertion grooves 11 shown in FIGS. 8 and 9 and due to the fact that the insertion grooves 11 are axially aligned in the lateral direction with the V-groove 17, it is possible to insert the test sample 2 laterally into the chucking tool 1 without moving the chucking tool in the axial direction of the longitudinal central axis 7.

Referring again to FIGS. 1 and 2, the operation of the chucking tool 1 by a pressure medium will now be described. The cylindrical shaft 13 of the operating member 4 has secured to its downwardly facing free end, a piston 29 which divides the shouldered bore 9 into two chambers 30 and 31. The piston 29 is secured to the free end of the cylindrical shaft 13 by screws 29A. The lower chamber 31 is closed by a cover 28 secured to the housing 3 by screws 28A. Fluid under pressure is introduced into the chamber 30 through an inlet port 30A. Fluid under pressure is introduced into the chamber 31 through a port 31A. The piston 29 has a large surface 29B facing the cover 28 and a smaller ring surface 29C around the cylindrical shaft 13.

The clamping force is released by applying fluid under pressure to the ring surface 29C in the chamber 30, whereby the operating member 4 moves downwardly in the direction of the arrow 32. In the end position of the operating member 4 in which no force is applied to the jaws 5, 5A, the operating member 4 assumes the position shown in FIGS. 1 and 2. Before reaching the lowermost position the jaws move away from each other radially outwardly, due to the guiding by the guide arms 26 and due to the guiding of the guide member 21 in the groove 19. On the other hand, when fluid under pressure is introduced into the chamber 31, thereby applying pressure to the surface 29B, the operating member 4 moves upwardly in the direction of the arrow 33, while the jaws remain axially stationary, but are forced to move radially inwardly. The radial inward and outward movement is indicated by the arrow 27 in FIG. 1. Thus, the axial movement of the operating member 24 is converted into a radial movement of the jaws 5, 5A by the cooperation of the slanted surfaces 18 of the operating member 4, and the slanted surfaces 20 of the jaws. The pressure release from the chambers 30 and 31 may take place through the same ports 30A and 31A through which fluid under pressure is introduced into these chambers.

Although the invention has been described with reference to specific example embodiments, it will be appreciated that it is intended to cover all modifications and equivalents within the scope of the appended claims.

What I claim is:

1. A chucking tool for holding a work piece with a wedging action, comprising a clamping housing (3) having a central longitudinal axis (7), at least one clamping jaw (5) in said clamping housing with a movement component perpendicularly to said central axis, means (26) for preventing movement of said clamping jaw (5) in a direction coaxial to said central longitudinal axis (7) of said clamping housing (3) while permitting said movement component of said clamping jaw perpendicular to said central longitudinal axis, an operating member (4) guided in said clamping housing (3) for movement coaxially to said central longitudinal axis (7), said operating member (4) having at least one first slanted surface (18), said at least one clamping jaw having a second slanted surface (20) cooperating with said first slanted surface (18) of said operating member (4), said second slanted surface (20) of said at least one clamping jaw having a slant toward a clamped end of said work piece, a force application device for moving said operating member (4) coaxially with said central longitudinal axis for driving said at least one clamping jaw (5) into a position clamping said work piece with said wedging action and for releasing said wedging action, and wherein said clamping housing (3) and said operating member (4) have respective lateral access means (11, 17) for insertion of said work piece laterally into a clamping position.

2. The chucking tool of claim 1, wherein said force application device comprises a piston cylinder (29, 9) for moving said operating member (4) in said clamping housing coaxially to said central longitudinal axis in one direction and in the opposite direction.

3. The chucking tool of claim 2, wherein said piston cylinder (29, 9) has an end portion forming a piston rod (13) as part of said operating member, said piston cylinder further comprising a piston (29) secured to a free end of said piston rod (13), said clamping housing having a first central bore (8) in which said piston rod (13) is slidingly guided, and a second bore (9) in which said piston (29) is slidingly received, said piston (29) dividing said second bore into two chambers for admitting a fluid under pressure to move said operating member.

4. The chucking tool of claim 1, comprising two clamping jaws (5, 5A) cooperating with each other for holding said work piece coaxially with said central longitudinal axis.

5. The chucking tool of claim 4, wherein each of said two clamping jaws comprises a respective clamping surface, each clamping device having grooves and ridges for an improved grip of said piece, said clamping surfaces extending in parallel to each other.

6. The chucking tool of claim 1, wherein said means for preventing movement of said clamping jaws in a direction coaxial to said central longitudinal axis comprise lateral arms (26) connected to said clamping housing and engaging said at least one clamping jaw so that said at least one clamping jaw is also prevented from rotating around said central longitudinal axis but permitted to move perpendicularly to said central longitudinal axis.

7. The chucking tool of claim 1, wherein said at least one clamping jaw comprises a first guide element, and wherein said operating member comprises a second guide element cooperating with said first guide element for permitting an axial movement of said operating member (4) relative to said at least one clamping jaw for applying a wedging force to said at least one clamping jaw and for releasing said at least one clamping jaw from said wedging force.

8. The chucking tool of claim 7, wherein said first and second guide elements have cooperating T-cross-sectional areas.

9. The chucking tool of claim 8, wherein one of said first and second guide elements is a rail with a T-cross-section and the other of said first and second guide elements is a groove with a respective T-cross-section, said rail being guided in said groove.

10. The chucking tool of claim 1, comprising two clamping jaws (5, 5A) having clamping surfaces extending in parallel to each other and facing each other, each clamping jaw having its respective slanted surface (20), and wherein said operating member (4) comprises two slanted surfaces (18) forming together a V-groove (17), said two clamping jaws being received in said V-groove (17), and wherein said slanting surfaces (20) of said two clamping jaws slant toward a clamped end of said work piece to form a V-configuration fitting into said V-groove.

11. The chucking tool of claim 10, further comprising a first guide elements in said slanted surfaces (20) of said operating member and a second guide elements in said slanted surfaces of said clamping jaws, said first and second guide means cooperating with each other for permitting said operating member to move relative to said clamping jaws to apply said wedging action and to release said wedging action.

12. The chucking tool of claim 11, wherein said first and second guide elements comprise guide grooves with a T-cross-section and guide rails with a T-cross-section received in said guide grooves.

13. The chucking tool of claim 3, wherein said piston has a first surface facing said piston rod and a second surface facing away from said piston rod, said first surface being smaller than said second larger surface and wherein said first and second surfaces are so arranged that pressure on said smaller surface opens said at least one clamping jaw and pressure on said second larger surface closes said at least one clamping jaw for a clamping action.

* * * * *

UNITED STATES PATENT AND TRADEMARK OFFICE
CERTIFICATE OF CORRECTION

PATENT NO. : 5,322,301
DATED : June 21, 1994
INVENTOR(S) : Andreas Pohl

It is certified that error appears in the above-indentified patent and that said Letters Patent is hereby corrected as shown below:

Column 7, line 57, repalce "device" by --surface--.

Column 8, line 42, repalce "means" by --elements--.

Signed and Sealed this

Eleventh Day of October, 1994

Attest:

BRUCE LEHMAN

Attesting Officer    Commissioner of Patents and Trademarks